United States Patent [19]

Meyer

[11] 4,030,480

[45] June 21, 1977

[54] OCULAR DECOMPRESSION PROCESS

[76] Inventor: Ernst Jochen Meyer, 174 School St., Belmont, Mass. 02178

[22] Filed: May 13, 1976

[21] Appl. No.: 686,056

[52] U.S. Cl. .............................. 128/1.5; 128/303.1; 128/410

[51] Int. Cl.$^2$ .................. A61B 17/38; A61N 1/42; A61F 9/00

[58] Field of Search ................. 128/1.3, 1.5, 303.1, 128/410

[56] References Cited

UNITED STATES PATENTS 3,419,008  12/1968  Plishner ..................... 128/1 R X

FOREIGN PATENTS OR APPLICATIONS 1,284,528  12/1968  Germany ..................... 128/1.5

Primary Examiner—Channing L. Pace

[57] ABSTRACT

This ocular decompression process is a surgical procedure and a physical therapy for the alleviation of glaucoma. The invention contemplates a surgical operation on the eye, at which a metallic implant is introduced through the sclera into or adjacent to the anterior chamber of the eye. The extra-cameral portion of the implant, fashioned into a loop, is buried under fibrous and epithelial tissue. After the surgical incisions have healed, the coil of a tuned radio-frequency circuit is brought into the field of the implant by being positioned exterior to the eye. The implanted wire acts as the secondary of a radio-frequency transformer and generates heat sufficient to create a tract from the anterior chamber to the subconjunctival tissue. This tract serves as a drain through which the aqueous humor flows from the inside of the eye to its surface, thereby reducing the pathologically elevated intraocular pressure. The application of radio-frequency energy to the implant may be repeated as necessary to maintain satisfactory tension.

1 Claim, 1 Drawing Figure

OCULAR DECOMPRESSION PROCESS

BRIEF SUMMARY OF THE INVENTION

This invention is an ophthalmologic surgical operation and post-operative physical therapy for the alleviation or cure of glaucoma and is distinguished from conventional procedures for this purpose by its utilization of the well-established but hitherto unexploited principle that radio-frequency energy may be transmitted across an intact tissue barrier to produce critically localized and accurately controllable destruction of tissue in the immediate vicinity of a previously implanted metallic conductor.

Glaucoma, a disease frequently destructive of eyesight, is a disorder of the hydrostatic servomechanism of the eye, where, given a relatively constant inflow of fluid into a sphere of fixed volume, there develops a pressure which is directly proportional to the outflow resistance; and numerous surgical operations, collectively designated as filtering procedures, have been devised for diminishing the abnormally increased resistance to fluid outflow from the eye and thereby reducing pathologically elevated intraocular pressure.

Conventional filtering operations involve the perforation of the eye by linear incision, cautery, punch, or trephine, but inasmuch as the existence of an open fistula is incompatible with the survival of the eye, the perforation is no sooner made than it is partially occluded by a covering of fibrous and epithelial tissues. When filtering operations are successful, these delicate tissues form a diffuse, thin-walled scar which permits the escape of the aqueous humor either into the tear film or into the contiguous lymphatic or capillary circulation.

As they are conventionally performed, filtering operations for glaucoma have the following major disadvantages: (1) The initial perforation of the eyeball causes an uncontrolled flow of fluid from the eye, frequently leading to a partial collapse of the eyeball and a consequent disarrangement of the internal structures of the eye, termed by physicians as flat anterior chamber with choroidal separation, and requiring one or more delicate and dangerous reoperations within two or three weeks of the original procedure. (2) As the tissues heal, excessive scar formation frequently leads to occlusion of the drainage channel and the consequent failure of the operation. (3) Where the operation is successful and a functioning filtering scar is obtained, the same channel that permits the egress of fluid, facilitates invasion of the eyeball by pathogenic bacteria, so that a destructive infection of the eye is a not uncommon complication of successful filtering surgery. (4) Conventional filtering operations constitute a major surgical trauma to the eye, often resulting in chronic inflammation and cataract formation, thus precipitating a chain of events by which, even if the eye is saved from glaucoma, the eyesight is severely impaired.

For all these reasons, conventional filtering operations for glaucoma are relied upon only as a last resort when glaucomatous damage to the vision has been conclusively documented and when such operations offer the only alternative to the certain, if gradual, onset of blindness. Even then, the overall success rate of filtering operations is probably little better than 70%, and of eyes where the initial operation failed, only a fraction are saved by repeated surgery.

The present invention provides a method for creating a drainage fistula free of the aforementioned complications. To this end, the invention contemplates the implantation into the wall of the eye of a metallic wire or ribbon which enters or abuts the anterior chamber of the eye, and which, fashioned into a loop, may, at repeated intervals after the original operation, be heated with induced radio-frequency currents of appropriate amplitude, wavelength, and duration. These radio frequency currents are impressed upon the buried implant through an external coil, incorporated into a tuned inductive-capacitative circuit, and positioned immediately in front of the eye, which coil has itself been energized with radio-frequency current. Inasmuch as the initial implantation, skilfully performed, involves only slight trauma to the eye, and inasmuch as the radio-frequency energy may be applied in a controlled, graded manner over a period of time, this invention makes possible the establishment of a drainage fistula with a minimum of trauma, a minimum of complication, and a maximum of efficacy.

Accordingly, the object of this invention is the creation of a drainage fistula for the alleviation or cure of glaucoma.

A further object of this invention is, in the establishing of the aforementioned drainage fistula, the avoidance of the sudden elimination of all resistance to outflow which accompanies the initial stages of the conventional operations and often leads to flat anterior chamber and choroidal separation.

A further object is, in the establishing of the aforementioned fistula, the provision of a means, short of reoperation, for re-establishing outflow channels that have been constricted by scar formation.

A further object is the creation of drainage channels at levels below the surface of the eyeball where they will be less vulnerable to external infection.

A further object is the reduction of surgical trauma required to obtain the necessary drainage.

A further object is to increase the percentage of successful glaucoma operations.

A further object is to provide an effective surgical treatment for glaucoma in situations such as juvenile glaucoma, inflammatory glaucoma, or post-surgical glaucoma, where conventional procedures are unlikely to be successful.

A further object is to decrease the length of disability and hospitalization occasioned by glaucoma operations.

A further object is to make glaucoma operations relatively more safe and effective, so that many patients now committed to the lifelong use of topical medication might be enabled to benefit from surgical treatment.

Further objects and advantages of this invention will appear as the specification progresses.

DETAILED DESCRIPTION

Figure 1:
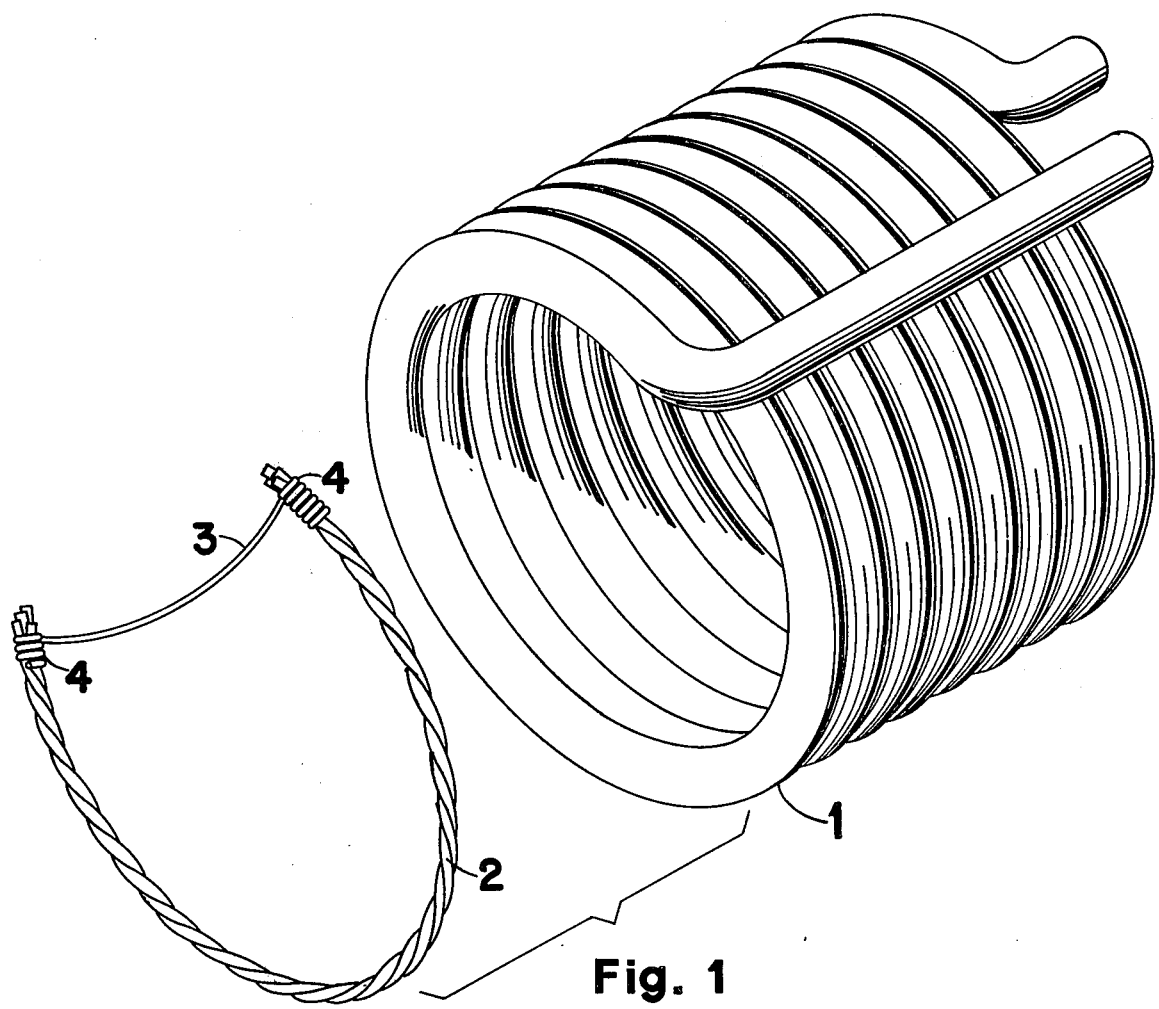
FIG. 1 is a perspective view of the exciting coil 1 and the metallic implant 2, 3, 4, in their spatial relationship during the heating process.

This invention entails a surgical operation and one or more therapeutic applications of radio-frequency current.

The technique of the surgical operation will unavoidably reflect not only the particularities of the deseased eye in its structure and function, but also the experience, skill, and judgments of the operating surgeon, and the specific embodiments hereinafter described shall not be construed as limiting the scope of the appended claims.

The preferred embodiment of the invention involves taking a patient to an operating room where the diseased eye is prepared and draped in the usual manner. Anesthesia and akinesia may be obtained by the systemic administration of drugs, or more frequently, by injection of local anesthetic agents into the lids and orbit by conventional techniques of retrobulbar anesthesia. A lid speculum is placed, and a bridle suture is threaded through the tendon of the superior rectus muscle. Factitious edema of the conjunctival tissues is then created by the subconjunctival infiltration through a small calibre hypodermic needle of appropriate quantities of sterile saline solution. A round-shafted discission knife, whose tip has been perforated with an 0.1 mm hole, is then threaded with a 20 cm. length of 0.05 mm stainless steel suture. The tip of the knife so prepared is then introduced into the edematous conjuctiva 5 or more mm. from the corneoscleral limbus, its tip advanced deep through fibrous tissue toward the limbus and into the anterior chamber. Once the tip of the knife is seen in the anterior chamber, the direction of its advancement is changed so that the tip forthwith exits from the anterior chamber through the corneoscleral limbus and surfaces again in edematous conjunctiva, the point of exit being more or less symmetrical with the point of entrance about a plane bisecting the eye in the antero-posterior direction. The sites at which the discission knife perforates the conjuctiva on entering and exiting from the eye are hereinafter referred to as the original conjunctival incisions. One limb of the stainless steel suture in the tip of the knife is now grasped with forceps, and a sufficient length of suture is pulled forward to permit the unimpeded withdrawal of the knife, which, having been removed from the eye is promptly freed from the other limb of the stainless steel suture. That suture now lies, double-stranded, in the tract made by the knife, two ends projecting from the original conjunctival entrance incision, and a loop projecting from the incision through which the knife first exited from the anterior chamber. The stainless steel loop is now threaded with the thermal electrode, being one or more strands of chemically inert wire such as platinum or platinum-iridium, or of ribbon, braid or cable of such metal, with a cross-sectional area ranging from $1 \times 10^{-4}$ to $8 \times 10^{-1}$ mm.$^2$, more or less. By means of the stainless steel suture, the thermal electrode is pulled through the anterior chamber, whereupon the stainless steel suture is discarded. A third wire, the antenna electrode hereinafter, being one or more strands of chemically inert wire such as platinum or platinum-iridium, with a cross-section greater than that of the thermal electrode, is now prepared. One end of the antenna electrode is introduced into one of the original conjunctival incisions to the episcleral space and is advanced under the insertions of those three recti muscles that are remoted from the thermal electrode. Having thus been threaded circumferentially around the eyeball, the end of the antenna electrode is extracted through the other of the original conjunctival incisions. Two electrodes have now been placed in the eye: the thermal electrode 3, FIG. 1, through the anterior chamber, and the antenna electrode 4, FIG. 1, circumferentially under the muscle insertions. One end of each of these electrodes now projects from each of the original incisions. The adjacent ends of the respective electrodes are now clamped or spliced, as shown in 4, FIG. 1. The conjoined wires are trimmed, and by means of forceps, are tucked deep into the fibrous tissue. The conjuctival incisions are each closed with an appropriate number of surgical sutures.

An alternative preferred embodiment involves the dissection of the conjuctival and scleral flap as is now customary in the operation known as trabeculectomy ab externo, and the implantation of the thermal electrode into the corneoscleral trabecular meshwork, without entering the anterior chamber. The thermal electrode is then spliced or clamped at each end to the adjacent end of an antenna electrode, placed as hereinabove described.

Another alternative preferred embodiment applies where, as in iridectomy or cataract extraction, a corneoscleral incision of substantial length is required. In such a situation, the thermal electrode may be placed in or through the aforesaid larger incision and covered with a previously prepared conjuctival flap, the antenna electrode having been placed in the above described manner prior to the opening of the anterior chamber.

Another preferred embodiment applies electively where higher radio-frequencies, in excess of 10 MHz more or less are employed. In such situations, the antenna electrode may be omitted, the two ends of the thermal electrode being spliced together to constitute a ring of perhaps 9 mm diameter, more or less.

Yet another preferred embodiment is applicable where such higher radio-frequencies are employed as hereinabove specified, when a combined thermal-antenna electrode may be pre-fabricated prior to surgery in the form of a ring of wire, braid, cable, or foil, one segment of which is placed into or through an ab externo corneoscleral incision into or abutting the anterior chamber, and covered with conjunctival and fibrous tissue as hereinabove described.

Heating of the implanted electrodes may be undertaken at any time after their placement, but preferably after a few days' interval has permitted the eye to heal somewhat from surgery. The preferred embodiment of the exciting coil is a helix of No. 14 B & S gauge insulated copper wire, nine turns having an air core 25 mm in diameter. An alternative preferred embodiment is a similar coil of elliptical cross-section to fit the shape of the patient's orbital rims. The dimensions of the coil are not critical, provided only that a sufficiently strong electromagnetic field is set up to produce the desired heating. The required inductance of the coil is, as is well known, a function of the frequency and of the reactive values of other portions of the circuit.

Radio-frequency energy may be provided by any one of numerous commerically available radio-frequency oscillators and amplifiers. One preferred embodiment utilizes a radio-frequency generator delivering 200 watts at 4 MHz. An alternative preferred embodiment uses any one of the various frequencies reserved by the Federal Communications Commission for medical and or surgical diathermy at about the same power of 200 watts. Yet a third preferred embodiment uses frequencies in excess of 30 MHz, permitting smaller electrode dimensions as well as an electrode configuration osculating with the corneal circumference rather than concentric with it, as hereinabove described.

Control of the heating process requires as a preferred embodiment, a timing device capable of limiting the applied radio-frequency energy to periods ranging upwards of 0.1 seconds. An additional preferred embodiment for measuring and controlling the electrical energy delivered to the eye is a field strength meter, whose antenna is in the immediate vicinity of the patient's eye, and a portion of whose output is used both to trigger the aforementioned timing device and to interrupt the power to the output stage of the radio-frequency generator when the field strength rises above a given, predetermined safe level.

What is claimed is:

1. A method for reducing intraocular pressure, comprising the following steps in the order listed, of which those designated (a), (f), (g) and (j) are conventional, and those designated (b), (c), (d), (e), (h), (i) and (k) are wherein the improvement comprises,
   a. inducing anesthesia
   b. introducing a metallic wire, band, or ring, hereinafter the thermal electrode, through or immediately adjacent to the anterior chamber of the eyeball in such manner that (i) the pupil of the eye is not obstructed, and (ii) those portions of the thermal electrode not within sclera or anterior chamber are everywhere covered by fibrous or epithelial tissues,
   c. introducing a second metallic band or wire, hereinafter the antenna electrode, of greater cross section than the thermal electrode, onto the surface of the surface of the sclera of the eyeball, in such manner (i) that the antenna electrode is everywhere covered by fibrous or epithelial tissues, (ii) that each of the ends of the antenna electrode overlaps one of the ends of the thermal electrode, (iii) that the antenna electrode forms more or less the arc of a circle, and (iv) that the circle described by the aforesaid arc is susceptible, by passive rotation of the eyeball, of being brought into a plane more or less parallel to the frontal plane of the face,
   d. connecting each end of any thermal electrode which is not a ring with that end of the antenna electrode which overlaps it, so as to establish a closed loop electrical circuit,
   e. connecting each end of any thermal electrode which is not a ring and which is not connected with an antenna electrode with the opposite end of that thermal electrode so as to form a closed loop electrical circuit,
   f. closing, by means of surgical sutures, the sites at which the thermal and antenna electrodes were introduced beneath the tissues, so that these electrodes and their junctions are everywhere covered by tissue and are nowhere exposed to air,
   g. infiltrating an aqueous solution under that portion of the conjunctiva which covers the thermal electrode,
   h. positioning, immediately anterior to the eyeball and more or less coaxial with the circle described by the electrode(s), an insulated induction coil which is wired into and is part of a tuned radio-frequency circuit,
   i. impressing upon the aforesaid induction coil, a radio-frequency voltage sufficient to induce a current in the circuit formed by the electrode(s), such that the segment of the thermal electrode which is not bathed in fluid becomes hot and by its heat creates a passage through which fluid may drain from the anterior chamber into the fibrous tissue on the surface of the eyeball,
   j. controlling the onset, intensity, and duration of the radio-frequency voltage by means of electronic measuring and timing devices.
   k. repeating steps (g), (h), (i), and (j) above at such intervals and for such periods of time as may be required to maintain a sufficient drainage of fluid from the eye.

* * * * *